(12) United States Patent
Malinowski

(10) Patent No.: US 12,390,340 B2
(45) Date of Patent: Aug. 19, 2025

(54) INTERSPINOUS SPACER WITH A RANGE OF DEPLOYMENT POSITIONS AND METHODS AND SYSTEMS

(71) Applicant: Boston Scientific Neuromodulation Corporation, Valencia, CA (US)

(72) Inventor: Zdzislaw Bernard Malinowski, Castaic, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 16 days.

(21) Appl. No.: 18/602,968

(22) Filed: Mar. 12, 2024

(65) Prior Publication Data

US 2024/0307189 A1    Sep. 19, 2024

Related U.S. Application Data

(60) Provisional application No. 63/452,249, filed on Mar. 15, 2023.

(51) Int. Cl.
*A61F 2/44* (2006.01)
*A61B 17/88* (2006.01)
(Continued)

(52) U.S. Cl.
CPC ........ *A61F 2/4425* (2013.01); *A61B 17/8888* (2013.01); *A61F 2/4611* (2013.01);
(Continued)

(58) Field of Classification Search
CPC .................. A61F 2/4455; A61F 2/4425; A61F 2220/0016; A61F 2220/0091; A61L 27/3658
(Continued)

(56) References Cited

U.S. PATENT DOCUMENTS 2,248,054 A   7/1941  Becker
2,677,369 A   5/1954  Knowles
(Continued)

FOREIGN PATENT DOCUMENTS

CA       268461     2/1927
CN      2794456     7/2006
(Continued)

OTHER PUBLICATIONS

ASNR Neuroradiology Patient Information website, Brain and Spine Imaging: A Patient's Guide to Neuroradiology; Myelography; http://www.asnr.org/patientinfo/procedures/myelography.shtml#sthash.sXIDOxWq.dpbs, Copyright 2012-2013.
(Continued)

*Primary Examiner* — Eduardo C Robert
(74) *Attorney, Agent, or Firm* — Branch Partners PLLC; Bruce E. Black

(57) ABSTRACT

An interspinous spacer includes a body having a channel and at least one slot; an arm actuator defining a threaded channel; an actuator screw including a shaft with a threaded distal portion partially disposed in the channel of the body and the threaded channel of the arm actuator; a first pin arranged to move along the slot of the body; a second pin; and first and second arms, each having a coupling extension that defines a pin opening and a curved track. The first and second arms are coupled to the body by the second pin extending through the curved tracks and further coupled to the body and the actuator arm by the first pin extending through the pin openings. The first and second arms rotate among different deployment positions according to the curved track in response to longitudinal movement of the actuator arm as the actuator screw is rotated.

20 Claims, 4 Drawing Sheets

(51) Int. Cl.
*A61F 2/46* (2006.01)
*A61F 2/30* (2006.01)

(52) U.S. Cl.
CPC .............. *A61F 2002/30405* (2013.01); *A61F 2002/30494* (2013.01); *A61F 2002/30495* (2013.01); *A61F 2002/30528* (2013.01); *A61F 2002/4615* (2013.01)

(58) Field of Classification Search
USPC ...................................................... 623/17.16
See application file for complete search history.

(56) References Cited

U.S. PATENT DOCUMENTS

| | | | |
|---|---|---|---|
| 2,933,114 A | 4/1960 | Bystrom |
| 3,242,120 A | 3/1966 | Steuber |
| 3,486,505 A | 12/1969 | Morrison |
| 3,648,691 A | 3/1972 | Lumb et al. |
| 3,780,733 A | 12/1973 | Martinez-Manzor |
| 3,986,383 A | 10/1976 | Petteys |
| 4,545,374 A | 10/1985 | Jacobson |
| 4,632,101 A | 12/1986 | Freeland |
| 4,685,447 A | 8/1987 | Iversen et al. |
| 4,799,484 A | 1/1989 | Smith et al. |
| 4,863,476 A | 9/1989 | Sheppard |
| 4,877,020 A | 10/1989 | Vich |
| 4,895,564 A | 1/1990 | Farrell |
| 4,986,831 A | 1/1991 | King et al. |
| 5,011,484 A | 4/1991 | Breard |
| 5,015,247 A | 5/1991 | Michelson |
| 5,019,081 A | 5/1991 | Watanabe |
| 5,040,542 A | 8/1991 | Gray |
| 5,059,193 A | 10/1991 | Kuslich |
| 5,092,866 A | 3/1992 | Breard et al. |
| 5,178,628 A | 1/1993 | Otsuka et al. |
| 5,180,393 A | 1/1993 | Commarmond |
| 5,182,281 A | 1/1993 | Frigola-Constansa et al. |
| 5,188,281 A | 2/1993 | Fujiwara et al. |
| 5,192,281 A | 3/1993 | de la Caffiniere |
| 5,195,526 A | 3/1993 | Michelson |
| 5,238,295 A | 8/1993 | Harrell |
| 5,298,253 A | 3/1994 | LeFiles et al. |
| 5,368,594 A | 11/1994 | Martin et al. |
| 5,390,683 A | 2/1995 | Pisharodi |
| 5,415,661 A | 5/1995 | Holmes |
| 5,456,722 A | 10/1995 | McLeod et al. |
| 5,462,738 A | 10/1995 | LeFiles et al. |
| 5,472,452 A | 12/1995 | Trott |
| 5,484,437 A | 1/1996 | Michelson |
| 5,487,739 A | 1/1996 | Aebischer et al. |
| 5,489,308 A | 2/1996 | Kuslich et al. |
| 5,496,318 A | 3/1996 | Howland et al. |
| 5,531,748 A | 7/1996 | de la Caffiniere |
| 5,549,679 A | 8/1996 | Kuslich |
| 5,571,189 A | 11/1996 | Kuslich |
| 5,591,165 A | 1/1997 | Jackson |
| 5,609,634 A | 3/1997 | Voydeville |
| 5,609,636 A | 3/1997 | Kohrs et al. |
| 5,645,599 A | 7/1997 | Samani |
| 5,654,599 A | 8/1997 | Casper |
| 5,658,335 A | 8/1997 | Allen |
| 5,658,337 A | 8/1997 | Kohrs et al. |
| 5,674,295 A | 10/1997 | Ray et al. |
| 5,700,264 A | 12/1997 | Zucherman et al. |
| 5,725,582 A | 3/1998 | Bevan et al. |
| 5,741,253 A | 4/1998 | Michelson |
| 5,746,720 A | 5/1998 | Stouder, Jr. |
| 5,762,629 A | 6/1998 | Kambin |
| 5,836,948 A | 11/1998 | Zucherman et al. |
| 5,860,977 A | 1/1999 | Zucherman et al. |
| 5,863,948 A | 1/1999 | Epstein et al. |
| 5,876,404 A | 3/1999 | Zucherman et al. |
| RE36,211 E | 5/1999 | Nonomura |
| 5,904,636 A | 5/1999 | Chen |
| 5,904,686 A | 5/1999 | Zucherman et al. |
| 5,928,207 A | 7/1999 | Pisano et al. |
| 5,948,017 A | 9/1999 | Taheri |
| 5,972,015 A | 10/1999 | Scribner et al. |
| 6,039,761 A | 3/2000 | Li et al. |
| 6,045,552 A | 4/2000 | Zucherman et al. |
| 6,048,342 A | 4/2000 | Zucherman et al. |
| 6,048,345 A | 4/2000 | Berke et al. |
| 6,066,154 A | 5/2000 | Reiley et al. |
| 6,068,630 A | 5/2000 | Zucherman et al. |
| 6,074,390 A | 6/2000 | Zucherman et al. |
| 6,080,155 A | 6/2000 | Michelson |
| 6,080,157 A | 6/2000 | Cathro et al. |
| 6,090,112 A | 7/2000 | Zucherman et al. |
| 6,096,038 A | 8/2000 | Michelson |
| 6,102,928 A | 8/2000 | Bonutti |
| 6,102,950 A | 8/2000 | Vaccaro |
| D433,193 S | 10/2000 | Gaw et al. |
| 6,132,464 A | 10/2000 | Martin |
| 6,149,642 A | 11/2000 | Gerhart et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,159,215 A | 12/2000 | Urbahns et al. |
| 6,179,873 B1 | 1/2001 | Zientek |
| 6,183,471 B1 | 2/2001 | Zucherman et al. |
| 6,190,387 B1 | 2/2001 | Zucherman et al. |
| 6,225,048 B1 | 5/2001 | Soderberg-Naucler et al. |
| 6,235,030 B1 | 5/2001 | Zucherman et al. |
| 6,238,397 B1 | 5/2001 | Zucherman et al. |
| 6,264,651 B1 | 7/2001 | Underwood et al. |
| 6,264,656 B1 | 7/2001 | Michelson |
| 6,267,763 B1 | 7/2001 | Castro |
| 6,267,765 B1 | 7/2001 | Taylor et al. |
| 6,270,498 B1 | 8/2001 | Michelson |
| 6,280,444 B1 | 8/2001 | Zucherman et al. |
| 6,312,431 B1 | 11/2001 | Asfora |
| 6,328,730 B1 | 12/2001 | Harkrider, Jr. |
| 6,332,882 B1 | 12/2001 | Zucherman et al. |
| 6,332,883 B1 | 12/2001 | Zucherman et al. |
| 6,336,930 B1 | 1/2002 | Stalcup et al. |
| 6,348,053 B1 | 2/2002 | Cachia |
| 6,364,883 B1 | 4/2002 | Santilli |
| 6,371,989 B1 | 4/2002 | Chauvin et al. |
| 6,375,682 B1 | 4/2002 | Fleischmann et al. |
| 6,379,355 B1 | 4/2002 | Zucherman et al. |
| 6,387,130 B1 | 5/2002 | Stone et al. |
| 6,395,032 B1 | 5/2002 | Gauchet |
| 6,402,740 B1 | 6/2002 | Ellis et al. |
| 6,402,750 B1 | 6/2002 | Atkinson et al. |
| 6,402,784 B1 | 6/2002 | Wardlaw |
| 6,413,228 B1 | 7/2002 | Hung et al. |
| 6,419,676 B1 | 7/2002 | Zucherman et al. |
| 6,419,677 B2 | 7/2002 | Zucherman et al. |
| 6,440,169 B1 | 8/2002 | Elberg et al. |
| 6,443,988 B2 | 9/2002 | Felt et al. |
| 6,447,547 B1 | 9/2002 | Michelson |
| 6,451,019 B1 | 9/2002 | Zucherman et al. |
| 6,451,020 B1 | 9/2002 | Zucherman et al. |
| 6,464,682 B1 | 10/2002 | Snoke |
| 6,471,976 B1 | 10/2002 | Taylor et al. |
| 6,478,796 B2 | 11/2002 | Zucherman et al. |
| 6,478,822 B1 | 11/2002 | Leroux et al. |
| 6,500,178 B2 | 12/2002 | Zucherman et al. |
| 6,514,256 B2 | 2/2003 | Zucherman et al. |
| 6,530,925 B2 | 3/2003 | Boudard et al. |
| 6,558,333 B2 | 5/2003 | Gilboa et al. |
| 6,565,570 B2 | 5/2003 | Sterett et al. |
| 6,572,617 B1 | 6/2003 | Senegas |
| 6,575,981 B1 | 6/2003 | Boyd et al. |
| 6,579,281 B2 | 6/2003 | Palmer et al. |
| 6,579,319 B2 | 6/2003 | Goble et al. |
| 6,582,433 B2 | 6/2003 | Yun |
| 6,582,451 B1 | 6/2003 | Marucci et al. |
| 6,599,292 B1 | 7/2003 | Ray |
| 6,602,248 B1 | 8/2003 | Sharps et al. |
| 6,610,065 B1 | 8/2003 | Branch et al. |
| 6,610,091 B1 | 8/2003 | Reiley |
| 6,616,673 B1 | 9/2003 | Stone et al. |

(56) References Cited

U.S. PATENT DOCUMENTS

| | | |
|---|---|---|
| 6,626,944 B1 | 9/2003 | Taylor |
| 6,645,207 B2 | 11/2003 | Dixon et al. |
| 6,645,211 B2 | 11/2003 | Magana |
| 6,652,527 B2 | 11/2003 | Zucherman et al. |
| 6,652,534 B2 | 11/2003 | Zucherman et al. |
| 6,663,637 B2 | 12/2003 | Dixon et al. |
| 6,679,886 B2 | 1/2004 | Weikel et al. |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,702,847 B2 | 3/2004 | Dicarlo |
| 6,712,819 B2 | 3/2004 | Zucherman et al. |
| 6,716,215 B1 | 4/2004 | David et al. |
| 6,716,245 B2 | 4/2004 | Pasquel et al. |
| 6,723,126 B1 * | 4/2004 | Berry .................. A61F 2/4455 606/247 |
| 6,726,690 B2 | 4/2004 | Eckman |
| 6,733,534 B2 | 5/2004 | Sherman |
| 6,746,485 B1 | 6/2004 | Zucherman et al. |
| 6,761,720 B1 | 7/2004 | Senegas |
| 6,783,529 B2 | 8/2004 | Hover et al. |
| 6,783,546 B2 | 8/2004 | Zucherman et al. |
| 6,796,983 B1 | 9/2004 | Zucherman et al. |
| 6,805,697 B1 | 10/2004 | Helm et al. |
| 6,835,205 B2 | 12/2004 | Atkinson et al. |
| 6,840,944 B2 | 1/2005 | Suddaby |
| 6,858,029 B2 | 2/2005 | Yeh |
| 6,869,398 B2 | 3/2005 | Obenchain et al. |
| 6,875,212 B2 | 4/2005 | Shaolian et al. |
| 6,902,566 B2 | 6/2005 | Zucherman et al. |
| 6,926,728 B2 | 8/2005 | Zucherman et al. |
| 6,946,000 B2 | 9/2005 | Senegas et al. |
| 6,949,123 B2 | 9/2005 | Reiley |
| 6,966,930 B2 | 11/2005 | Amin et al. |
| 6,974,478 B2 | 12/2005 | Reiley et al. |
| 6,976,988 B2 | 12/2005 | Ralph et al. |
| 7,011,685 B2 | 3/2006 | Arnin et al. |
| 7,029,473 B2 | 4/2006 | Zucherman et al. |
| 7,033,358 B2 | 4/2006 | Taylor et al. |
| 7,048,736 B2 | 5/2006 | Robinson et al. |
| 7,070,598 B2 | 7/2006 | Lim et al. |
| 7,083,649 B2 | 8/2006 | Zucherman et al. |
| 7,087,055 B2 | 8/2006 | Lim et al. |
| 7,087,083 B2 | 8/2006 | Pasquel et al. |
| 7,097,648 B1 | 8/2006 | Globerman et al. |
| 7,101,375 B2 | 9/2006 | Zucherman et al. |
| 7,163,558 B2 | 1/2007 | Senegas et al. |
| 7,179,225 B2 | 2/2007 | Shluzas et al. |
| 7,187,064 B2 | 3/2007 | Tzu et al. |
| 7,189,234 B2 | 3/2007 | Zucherman et al. |
| 7,189,236 B2 | 3/2007 | Taylor et al. |
| 7,201,751 B2 | 4/2007 | Zucherman et al. |
| 7,217,291 B2 | 5/2007 | Zucherman et al. |
| 7,223,289 B2 | 5/2007 | Trieu et al. |
| 7,229,441 B2 | 6/2007 | Trieu et al. |
| 7,238,204 B2 | 7/2007 | Le Couedic et al. |
| 7,252,673 B2 | 8/2007 | Lim |
| 7,273,496 B2 | 9/2007 | Mitchell |
| 7,282,063 B2 | 10/2007 | Cohen et al. |
| 7,297,162 B2 | 11/2007 | Mujwid |
| 7,306,628 B2 | 12/2007 | Zucherman et al. |
| 7,318,839 B2 | 1/2008 | Malberg et al. |
| 7,320,707 B2 | 1/2008 | Zucherman et al. |
| 7,335,200 B2 | 2/2008 | Carli |
| 7,335,203 B2 | 2/2008 | Winslow et al. |
| 7,354,453 B2 | 4/2008 | McAfee |
| 7,384,340 B2 | 6/2008 | Eguchi et al. |
| 7,390,330 B2 | 6/2008 | Harp |
| 7,410,501 B2 | 8/2008 | Michelson |
| 7,442,208 B2 | 10/2008 | Mathieu et al. |
| 7,445,637 B2 | 11/2008 | Taylor |
| 7,473,268 B2 | 1/2009 | Zucherman et al. |
| 7,476,251 B2 | 1/2009 | Zucherman et al. |
| 7,481,839 B2 | 1/2009 | Zucherman et al. |
| 7,481,840 B2 | 1/2009 | Zucherman et al. |
| 7,491,204 B2 | 2/2009 | Marnay et al. |
| 7,497,859 B2 | 3/2009 | Zucherman et al. |
| 7,503,935 B2 | 3/2009 | Zucherman et al. |
| 7,504,798 B2 | 3/2009 | Kawada et al. |
| 7,510,567 B2 | 3/2009 | Zucherman et al. |
| 7,520,887 B2 | 4/2009 | Maxy et al. |
| 7,520,899 B2 | 4/2009 | Zucherman et al. |
| 7,547,308 B2 | 6/2009 | Bertagnoli et al. |
| 7,549,999 B2 | 6/2009 | Zucherman et al. |
| 7,550,009 B2 | 6/2009 | Amin et al. |
| 7,565,259 B2 | 7/2009 | Sheng et al. |
| 7,572,276 B2 | 8/2009 | Lim et al. |
| 7,575,600 B2 | 8/2009 | Zucherman et al. |
| 7,585,313 B2 | 9/2009 | Kwak et al. |
| 7,585,316 B2 | 9/2009 | Trieu |
| 7,588,588 B2 | 9/2009 | Spitler et al. |
| 7,591,851 B2 | 9/2009 | Winslow et al. |
| 7,601,170 B2 | 10/2009 | Winslow et al. |
| 7,621,939 B2 | 11/2009 | Zucherman et al. |
| 7,635,377 B2 | 12/2009 | Zucherman et al. |
| 7,635,378 B2 | 12/2009 | Zucherman et al. |
| 7,637,950 B2 | 12/2009 | Baccelli et al. |
| 7,658,752 B2 | 2/2010 | Labrom et al. |
| 7,662,187 B2 | 2/2010 | Zucherman et al. |
| 7,666,186 B2 | 2/2010 | Harp |
| 7,666,209 B2 | 2/2010 | Zucherman et al. |
| 7,666,228 B2 | 2/2010 | Le Couedic et al. |
| 7,670,377 B2 | 3/2010 | Zucherman et al. |
| 7,682,376 B2 | 3/2010 | Trieu |
| 7,691,146 B2 | 4/2010 | Zucherman et al. |
| 7,695,513 B2 | 4/2010 | Zucherman et al. |
| 7,699,852 B2 | 4/2010 | Frankel et al. |
| 7,699,873 B2 | 4/2010 | Stevenson et al. |
| D618,796 S | 6/2010 | Cantu |
| 7,727,233 B2 | 6/2010 | Blackwell et al. |
| 7,727,241 B2 | 6/2010 | Gorensek et al. |
| 7,731,751 B2 | 6/2010 | Butler et al. |
| 7,742,795 B2 | 6/2010 | Stone et al. |
| 7,749,231 B2 | 7/2010 | Bonvallet et al. |
| 7,749,252 B2 | 7/2010 | Zucherman et al. |
| 7,749,253 B2 | 7/2010 | Zucherman et al. |
| 7,753,938 B2 | 7/2010 | Aschmann et al. |
| 7,758,619 B2 | 7/2010 | Zucherman et al. |
| 7,758,647 B2 | 7/2010 | Amin et al. |
| 7,763,028 B2 | 7/2010 | Lim et al. |
| 7,763,050 B2 | 7/2010 | Winslow et al. |
| 7,763,051 B2 | 7/2010 | Labrom et al. |
| 7,763,073 B2 | 7/2010 | Hawkins et al. |
| 7,763,074 B2 | 7/2010 | Altarac et al. |
| 7,766,967 B2 | 8/2010 | Francis |
| 7,776,090 B2 | 8/2010 | Winslow et al. |
| 7,780,709 B2 | 8/2010 | Bruneau et al. |
| 7,789,898 B2 | 9/2010 | Peterman |
| 7,794,476 B2 | 9/2010 | Wisnewski |
| 7,803,190 B2 | 9/2010 | Zucherman et al. |
| 7,806,911 B2 | 10/2010 | Peckham |
| 7,811,308 B2 | 10/2010 | Amin et al. |
| 7,811,322 B2 | 10/2010 | Amin et al. |
| 7,811,323 B2 | 10/2010 | Amin et al. |
| 7,811,324 B2 | 10/2010 | Amin et al. |
| 7,811,330 B2 | 10/2010 | Amin et al. |
| 7,819,921 B2 | 10/2010 | Grotz |
| 7,828,822 B2 | 11/2010 | Zucherman et al. |
| 7,828,849 B2 | 11/2010 | Lim |
| 7,833,272 B2 | 11/2010 | Amin et al. |
| 7,837,687 B2 | 11/2010 | Harp |
| 7,837,688 B2 | 11/2010 | Boyer et al. |
| 7,837,700 B2 | 11/2010 | Harp |
| 7,837,711 B2 | 11/2010 | Bruneau et al. |
| 7,837,734 B2 | 11/2010 | Zucherman et al. |
| 7,846,183 B2 | 12/2010 | Blain |
| 7,846,185 B2 | 12/2010 | Carls et al. |
| 7,846,186 B2 | 12/2010 | Taylor |
| 7,857,815 B2 | 12/2010 | Zucherman et al. |
| 7,862,569 B2 | 1/2011 | Zucherman et al. |
| 7,862,586 B2 | 1/2011 | Malek |
| 7,862,590 B2 | 1/2011 | Lim et al. |
| 7,862,592 B2 | 1/2011 | Peterson et al. |
| 7,862,615 B2 | 1/2011 | Carli et al. |

(56) References Cited

U.S. PATENT DOCUMENTS

| | | | |
|---|---|---|---|
| 7,867,276 B2 | 1/2011 | Matge et al. |
| 7,871,426 B2 | 1/2011 | Chin et al. |
| 7,896,879 B2 | 3/2011 | Solsberg et al. |
| 7,942,830 B2 | 5/2011 | Solsberg et al. |
| 7,955,392 B2 | 6/2011 | Dewey et al. |
| 7,985,246 B2 | 7/2011 | Trieu et al. |
| 8,012,207 B2 | 9/2011 | Kim |
| 8,025,684 B2 | 9/2011 | Garcia-Bengochea et al. |
| 8,057,513 B2 | 11/2011 | Kohm et al. |
| 8,062,332 B2 | 11/2011 | Cunningham et al. |
| 8,100,823 B2 | 1/2012 | Harp |
| 8,123,782 B2 | 2/2012 | Altarac et al. |
| 8,123,807 B2 | 2/2012 | Kim |
| 8,128,662 B2 | 3/2012 | Altarac et al. |
| 8,152,837 B2 | 4/2012 | Altarac et al. |
| 8,167,944 B2 | 5/2012 | Kim |
| 8,226,690 B2 | 7/2012 | Altarac et al. |
| 8,273,108 B2 | 9/2012 | Altarac et al. |
| 8,277,488 B2 | 10/2012 | Altarac et al. |
| 8,292,922 B2 | 10/2012 | Altarac et al. |
| 8,317,864 B2 | 11/2012 | Kim |
| 8,409,282 B2 | 4/2013 | Kim |
| 8,425,559 B2 | 4/2013 | Tebbe et al. |
| 8,523,909 B2 * | 9/2013 | Hess ................ A61B 17/7065 606/248 |
| 8,608,762 B2 | 12/2013 | Solsberg et al. |
| 8,613,747 B2 | 12/2013 | Altarac et al. |
| 8,628,574 B2 | 1/2014 | Altarac et al. |
| 8,696,671 B2 | 4/2014 | Solsberg et al. |
| 8,734,477 B2 | 5/2014 | Solsberg et al. |
| 8,740,948 B2 | 6/2014 | Reglos et al. |
| 8,845,726 B2 | 9/2014 | Tebbe et al. |
| 8,864,828 B2 | 10/2014 | Altarac et al. |
| 8,882,772 B2 | 11/2014 | Solsberg et al. |
| 8,894,653 B2 | 11/2014 | Solsberg et al. |
| 8,900,271 B2 | 12/2014 | Kim |
| 8,945,183 B2 | 2/2015 | Altarac et al. |
| 9,023,084 B2 | 5/2015 | Kim |
| 9,039,742 B2 | 5/2015 | Altarac et al. |
| 9,119,680 B2 | 9/2015 | Altarac et al. |
| 9,125,692 B2 | 9/2015 | Kim |
| 9,155,570 B2 | 10/2015 | Altarac et al. |
| 9,155,572 B2 | 10/2015 | Altarac et al. |
| 9,161,783 B2 | 10/2015 | Altarac et al. |
| 9,186,186 B2 | 11/2015 | Reglos et al. |
| 9,211,146 B2 | 12/2015 | Kim |
| 9,283,005 B2 | 3/2016 | Tebbe et al. |
| 9,314,279 B2 | 4/2016 | Kim |
| 9,393,055 B2 | 7/2016 | Altarac et al. |
| 9,445,843 B2 | 9/2016 | Altarac et al. |
| 9,532,812 B2 | 1/2017 | Altarac et al. |
| 9,572,603 B2 | 2/2017 | Altarac et al. |
| 9,675,303 B2 | 6/2017 | Choi |
| 9,861,398 B2 | 1/2018 | Altarac et al. |
| 9,956,011 B2 | 5/2018 | Altarac et al. |
| 10,058,358 B2 | 8/2018 | Altarac et al. |
| 10,080,587 B2 | 9/2018 | Altarac et al. |
| 10,166,047 B2 | 1/2019 | Altarac et al. |
| 10,258,479 B2 | 4/2019 | Stewart et al. |
| 10,524,772 B2 | 1/2020 | Choi et al. |
| 10,610,267 B2 | 4/2020 | Altarac et al. |
| 10,653,456 B2 | 5/2020 | Altarac et al. |
| 10,835,295 B2 | 11/2020 | Altarac et al. |
| 10,835,297 B2 | 11/2020 | Altarac et al. |
| 11,013,539 B2 | 5/2021 | Altarac et al. |
| 11,229,461 B2 | 1/2022 | Altarac et al. |
| 2001/0031965 A1 | 10/2001 | Zucherman et al. |
| 2002/0022856 A1 | 2/2002 | Johnson et al. |
| 2002/0042607 A1 | 4/2002 | Palmer et al. |
| 2002/0116009 A1 | 8/2002 | Fraser et al. |
| 2002/0143331 A1 | 10/2002 | Zucherman et al. |
| 2002/0151977 A1 | 10/2002 | Paes et al. |
| 2003/0040746 A1 | 2/2003 | Mitchell et al. |
| 2003/0040753 A1 | 2/2003 | Daum et al. |
| 2003/0074075 A1 | 4/2003 | Thomas et al. |
| 2003/0083747 A1 | 5/2003 | Winterbottom et al. |
| 2003/0105466 A1 | 6/2003 | Ralph et al. |
| 2003/0135275 A1 | 7/2003 | Garcia et al. |
| 2003/0149438 A1 | 8/2003 | Nichols et al. |
| 2003/0153976 A1 | 8/2003 | Cauthen, III et al. |
| 2003/0176921 A1 | 9/2003 | Lawson |
| 2003/0220643 A1 | 11/2003 | Ferree |
| 2003/0220650 A1 | 11/2003 | Major et al. |
| 2003/0233098 A1 | 12/2003 | Markworth |
| 2004/0087947 A1 | 5/2004 | Lim et al. |
| 2004/0106997 A1 | 6/2004 | Lieberson |
| 2004/0106999 A1 | 6/2004 | Mathews |
| 2004/0148028 A1 | 7/2004 | Ferree et al. |
| 2004/0167625 A1 | 8/2004 | Beyar et al. |
| 2004/0220568 A1 | 11/2004 | Zucherman et al. |
| 2004/0225295 A1 | 11/2004 | Zubok et al. |
| 2004/0249378 A1 | 12/2004 | Saint Martin et al. |
| 2004/0260305 A1 | 12/2004 | Gorensek et al. |
| 2005/0021042 A1 | 1/2005 | Marnay et al. |
| 2005/0049708 A1 | 3/2005 | Atkinson et al. |
| 2005/0075634 A1 | 4/2005 | Zucherman et al. |
| 2005/0090822 A1 | 4/2005 | DiPoto |
| 2005/0101955 A1 | 5/2005 | Zucherman et al. |
| 2005/0125066 A1 | 6/2005 | McAfee |
| 2005/0143738 A1 | 6/2005 | Zucherman et al. |
| 2005/0165398 A1 | 7/2005 | Reiley |
| 2005/0192586 A1 | 9/2005 | Zucherman et al. |
| 2005/0192671 A1 | 9/2005 | Bao et al. |
| 2005/0209603 A1 | 9/2005 | Zucherman et al. |
| 2005/0209698 A1 | 9/2005 | Gordon |
| 2005/0216087 A1 | 9/2005 | Zucherman et al. |
| 2005/0228383 A1 | 10/2005 | Zucherman et al. |
| 2005/0228384 A1 | 10/2005 | Zucherman et al. |
| 2005/0228426 A1 | 10/2005 | Campbell |
| 2005/0245937 A1 | 11/2005 | Winslow |
| 2005/0278036 A1 | 12/2005 | Leonard et al. |
| 2006/0030860 A1 | 2/2006 | Peterman |
| 2006/0036258 A1 | 2/2006 | Zucherman et al. |
| 2006/0064107 A1 | 3/2006 | Bertagnoli et al. |
| 2006/0064165 A1 | 3/2006 | Zucherman et al. |
| 2006/0064166 A1 | 3/2006 | Zucherman et al. |
| 2006/0074431 A1 | 4/2006 | Sutton et al. |
| 2006/0084976 A1 | 4/2006 | Borgstrom et al. |
| 2006/0084983 A1 | 4/2006 | Kim |
| 2006/0084985 A1 | 4/2006 | Kim |
| 2006/0084988 A1 | 4/2006 | Kim |
| 2006/0084991 A1 | 4/2006 | Borgstrom et al. |
| 2006/0085069 A1 | 4/2006 | Kim |
| 2006/0085070 A1 | 4/2006 | Kim |
| 2006/0085074 A1 | 4/2006 | Raiszadeh |
| 2006/0089718 A1 | 4/2006 | Zucherman et al. |
| 2006/0122458 A1 | 6/2006 | Bleich |
| 2006/0122620 A1 | 6/2006 | Kim |
| 2006/0149254 A1 | 7/2006 | Lauryssen et al. |
| 2006/0149289 A1 | 7/2006 | Winslow et al. |
| 2006/0167416 A1 | 7/2006 | Mathis et al. |
| 2006/0195102 A1 | 8/2006 | Malandain |
| 2006/0217811 A1 | 9/2006 | Lambrecht et al. |
| 2006/0224159 A1 | 10/2006 | Anderson |
| 2006/0235386 A1 | 10/2006 | Anderson |
| 2006/0241597 A1 | 10/2006 | Mitchell et al. |
| 2006/0241614 A1 | 10/2006 | Bruneau et al. |
| 2006/0241757 A1 | 10/2006 | Anderson |
| 2006/0247623 A1 | 11/2006 | Anderson et al. |
| 2006/0247632 A1 | 11/2006 | Winslow et al. |
| 2006/0247633 A1 | 11/2006 | Winslow et al. |
| 2006/0247650 A1 | 11/2006 | Yerby et al. |
| 2006/0247658 A1 | 11/2006 | Pond, Jr. et al. |
| 2006/0247773 A1 | 11/2006 | Stamp |
| 2006/0264938 A1 | 11/2006 | Zucherman et al. |
| 2006/0264939 A1 | 11/2006 | Zucherman et al. |
| 2006/0265066 A1 | 11/2006 | Zucherman et al. |
| 2006/0265067 A1 | 11/2006 | Zucherman et al. |
| 2006/0271044 A1 | 11/2006 | Petrini et al. |
| 2006/0271049 A1 | 11/2006 | Zucherman et al. |
| 2006/0271055 A1 | 11/2006 | Thramann |
| 2006/0271061 A1 | 11/2006 | Beyar et al. |
| 2006/0271194 A1 | 11/2006 | Zucherman et al. |
| 2006/0276801 A1 | 12/2006 | Yerby et al. |

(56) References Cited

U.S. PATENT DOCUMENTS

| | | |
|---|---|---|
| 2006/0276897 A1 | 12/2006 | Winslow et al. |
| 2006/0282077 A1 | 12/2006 | Labrom et al. |
| 2006/0282078 A1 | 12/2006 | Labrom et al. |
| 2007/0016196 A1 | 1/2007 | Winslow et al. |
| 2007/0032790 A1 | 2/2007 | Aschmann et al. |
| 2007/0055237 A1 | 3/2007 | Edidin et al. |
| 2007/0055246 A1 | 3/2007 | Zucherman et al. |
| 2007/0073289 A1 | 3/2007 | Kwak et al. |
| 2007/0073292 A1 | 3/2007 | Kohm et al. |
| 2007/0100340 A1 | 5/2007 | Lange et al. |
| 2007/0100366 A1 | 5/2007 | Dziedzic et al. |
| 2007/0123863 A1 | 5/2007 | Winslow et al. |
| 2007/0123904 A1 | 5/2007 | Stad et al. |
| 2007/0161991 A1 | 7/2007 | Altarac et al. |
| 2007/0161993 A1 | 7/2007 | Lowery et al. |
| 2007/0173818 A1 | 7/2007 | Hestad et al. |
| 2007/0173821 A1 | 7/2007 | Trieu |
| 2007/0173822 A1 | 7/2007 | Bruneau et al. |
| 2007/0173823 A1 | 7/2007 | Dewey et al. |
| 2007/0173832 A1 | 7/2007 | Tebbe et al. |
| 2007/0173939 A1 | 7/2007 | Kim et al. |
| 2007/0179500 A1 | 8/2007 | Chin et al. |
| 2007/0185490 A1 | 8/2007 | Implicito |
| 2007/0191857 A1 | 8/2007 | Allard et al. |
| 2007/0191948 A1 | 8/2007 | Amin et al. |
| 2007/0191991 A1 | 8/2007 | Addink |
| 2007/0198045 A1 | 8/2007 | Morton et al. |
| 2007/0198091 A1 | 8/2007 | Boyer et al. |
| 2007/0203493 A1 | 8/2007 | Zucherman et al. |
| 2007/0203495 A1 | 8/2007 | Zucherman et al. |
| 2007/0203496 A1 | 8/2007 | Zucherman et al. |
| 2007/0203497 A1 | 8/2007 | Zucherman et al. |
| 2007/0203501 A1 | 8/2007 | Zucherman et al. |
| 2007/0208345 A1 | 9/2007 | Marnay et al. |
| 2007/0208346 A1 | 9/2007 | Marnay et al. |
| 2007/0208366 A1 | 9/2007 | Pellegrino et al. |
| 2007/0210018 A1 | 9/2007 | Wallwiener et al. |
| 2007/0225706 A1 | 9/2007 | Clark et al. |
| 2007/0225724 A1 | 9/2007 | Edmond |
| 2007/0225807 A1 | 9/2007 | Phan et al. |
| 2007/0225814 A1 | 9/2007 | Atkinson et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233077 A1 | 10/2007 | Khalili |
| 2007/0233081 A1 | 10/2007 | Pasquel et al. |
| 2007/0233082 A1 | 10/2007 | Chin et al. |
| 2007/0233083 A1 | 10/2007 | Abdou |
| 2007/0233084 A1 | 10/2007 | Betz et al. |
| 2007/0233088 A1 | 10/2007 | Edmond |
| 2007/0233089 A1 | 10/2007 | DiPoto et al. |
| 2007/0233096 A1 | 10/2007 | Garcia-Bengochea |
| 2007/0233098 A1 | 10/2007 | Mastrorio et al. |
| 2007/0233129 A1 | 10/2007 | Bertagnoli et al. |
| 2007/0250060 A1 | 10/2007 | Anderson et al. |
| 2007/0260245 A1 | 11/2007 | Malandain et al. |
| 2007/0265623 A1 | 11/2007 | Malandain et al. |
| 2007/0265624 A1 | 11/2007 | Zucherman et al. |
| 2007/0265625 A1 | 11/2007 | Zucherman et al. |
| 2007/0265626 A1 | 11/2007 | Seme |
| 2007/0270822 A1 | 11/2007 | Heinz |
| 2007/0270823 A1 | 11/2007 | Trieu et al. |
| 2007/0270824 A1 | 11/2007 | Lim et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0272259 A1 | 11/2007 | Allard et al. |
| 2007/0276368 A1 | 11/2007 | Trieu et al. |
| 2007/0276369 A1 | 11/2007 | Allard et al. |
| 2007/0276370 A1 | 11/2007 | Altarac et al. |
| 2007/0276372 A1 | 11/2007 | Malandain et al. |
| 2007/0276373 A1 | 11/2007 | Malandain |
| 2007/0276390 A1 | 11/2007 | Salsberg |
| 2007/0276493 A1 | 11/2007 | Malandain et al. |
| 2007/0276496 A1 | 11/2007 | Lange et al. |
| 2007/0276497 A1 | 11/2007 | Anderson |
| 2007/0276500 A1 | 11/2007 | Zucherman et al. |
| 2008/0015700 A1 | 1/2008 | Zucherman et al. |
| 2008/0021468 A1 | 1/2008 | Zucherman et al. |
| 2008/0021560 A1 | 1/2008 | Zucherman et al. |
| 2008/0021561 A1 | 1/2008 | Zucherman et al. |
| 2008/0027545 A1 | 1/2008 | Zucherman et al. |
| 2008/0027552 A1 | 1/2008 | Zucherman et al. |
| 2008/0027553 A1 | 1/2008 | Zucherman et al. |
| 2008/0033445 A1 | 2/2008 | Zucherman et al. |
| 2008/0033553 A1 | 2/2008 | Zucherman et al. |
| 2008/0033558 A1 | 2/2008 | Zucherman et al. |
| 2008/0033559 A1 | 2/2008 | Zucherman et al. |
| 2008/0039853 A1 | 2/2008 | Zucherman et al. |
| 2008/0039858 A1 | 2/2008 | Zucherman et al. |
| 2008/0039859 A1 | 2/2008 | Zucherman et al. |
| 2008/0039945 A1 | 2/2008 | Zucherman et al. |
| 2008/0039946 A1 | 2/2008 | Zucherman et al. |
| 2008/0039947 A1 | 2/2008 | Zucherman et al. |
| 2008/0045958 A1 | 2/2008 | Zucherman et al. |
| 2008/0045959 A1 | 2/2008 | Zucherman et al. |
| 2008/0046081 A1 | 2/2008 | Zucherman et al. |
| 2008/0046085 A1 | 2/2008 | Zucherman et al. |
| 2008/0046086 A1 | 2/2008 | Zucherman et al. |
| 2008/0046087 A1 | 2/2008 | Zucherman et al. |
| 2008/0046088 A1 | 2/2008 | Zucherman et al. |
| 2008/0051785 A1 | 2/2008 | Zucherman et al. |
| 2008/0051896 A1 | 2/2008 | Suddaby |
| 2008/0051898 A1 | 2/2008 | Zucherman et al. |
| 2008/0051899 A1 | 2/2008 | Zucherman et al. |
| 2008/0051904 A1 | 2/2008 | Zucherman et al. |
| 2008/0051905 A1 | 2/2008 | Zucherman et al. |
| 2008/0058806 A1 | 3/2008 | Klyce et al. |
| 2008/0058807 A1 | 3/2008 | Klyce et al. |
| 2008/0058808 A1 | 3/2008 | Klyce et al. |
| 2008/0058941 A1 | 3/2008 | Zucherman et al. |
| 2008/0065086 A1 | 3/2008 | Zucherman et al. |
| 2008/0065212 A1 | 3/2008 | Zucherman et al. |
| 2008/0065213 A1 | 3/2008 | Zucherman et al. |
| 2008/0065214 A1 | 3/2008 | Zucherman et al. |
| 2008/0071280 A1 | 3/2008 | Winslow |
| 2008/0071378 A1 | 3/2008 | Zucherman et al. |
| 2008/0071380 A1 | 3/2008 | Sweeney |
| 2008/0086212 A1 | 4/2008 | Zucherman et al. |
| 2008/0108990 A1 | 5/2008 | Mitchell et al. |
| 2008/0114455 A1 | 5/2008 | Lange et al. |
| 2008/0132952 A1 | 6/2008 | Malandain et al. |
| 2008/0167655 A1 | 7/2008 | Wang et al. |
| 2008/0167656 A1 | 7/2008 | Zucherman et al. |
| 2008/0167657 A1 | 7/2008 | Greenhalgh |
| 2008/0172057 A1 | 7/2008 | Zucherman et al. |
| 2008/0177271 A1 | 7/2008 | Yeh |
| 2008/0177272 A1 | 7/2008 | Zucherman et al. |
| 2008/0177306 A1 | 7/2008 | Lamborne et al. |
| 2008/0177312 A1 | 7/2008 | Perez-Cruet et al. |
| 2008/0183210 A1 | 7/2008 | Zucherman et al. |
| 2008/0188895 A1 | 8/2008 | Cragg et al. |
| 2008/0195152 A1 | 8/2008 | Altarac et al. |
| 2008/0208344 A1 | 8/2008 | Kilpela et al. |
| 2008/0215058 A1 | 9/2008 | Zucherman et al. |
| 2008/0221692 A1 | 9/2008 | Zucherman et al. |
| 2008/0228225 A1 | 9/2008 | Trautwein et al. |
| 2008/0234708 A1 | 9/2008 | Houser et al. |
| 2008/0234824 A1 | 9/2008 | Youssef et al. |
| 2008/0287997 A1 | 11/2008 | Altarac et al. |
| 2008/0288075 A1 | 11/2008 | Zucherman et al. |
| 2008/0319550 A1 | 12/2008 | Altarac et al. |
| 2009/0012528 A1 | 1/2009 | Aschmann et al. |
| 2009/0118833 A1 | 5/2009 | Hudgins et al. |
| 2009/0125030 A1 | 5/2009 | Tebbe et al. |
| 2009/0125036 A1 | 5/2009 | Bleich |
| 2009/0138046 A1 | 5/2009 | Altarac et al. |
| 2009/0138055 A1 | 5/2009 | Altarac et al. |
| 2009/0222043 A1 | 9/2009 | Altarac et al. |
| 2009/0248079 A1 | 10/2009 | Kwak et al. |
| 2009/0265007 A1* | 10/2009 | Colleran ............ A61F 2/4611 606/90 |

(56) References Cited

U.S. PATENT DOCUMENTS

| | | |
|---|---|---|
| 2009/0292315 A1 | 11/2009 | Trieu |
| 2009/0292316 A1 | 11/2009 | Hess |
| 2010/0042217 A1 | 2/2010 | Zucherman et al. |
| 2010/0082108 A1 | 4/2010 | Zucherman et al. |
| 2010/0114100 A1 | 5/2010 | Mehdizade |
| 2010/0131009 A1 | 5/2010 | Roebling et al. |
| 2010/0152775 A1* | 6/2010 | Seifert .............. A61B 17/3468 623/17.11 |
| 2010/0160947 A1 | 6/2010 | Akyuz et al. |
| 2010/0228092 A1 | 9/2010 | Ortiz et al. |
| 2010/0234889 A1 | 9/2010 | Hess |
| 2010/0262243 A1 | 10/2010 | Zucherman et al. |
| 2010/0280551 A1 | 11/2010 | Pool |
| 2010/0305611 A1 | 12/2010 | Zucherman et al. |
| 2011/0172710 A1 | 7/2011 | Thommen et al. |
| 2011/0245833 A1 | 10/2011 | Anderson |
| 2011/0313457 A1 | 12/2011 | Reglos et al. |
| 2012/0078301 A1 | 3/2012 | Hess |
| 2012/0158063 A1 | 6/2012 | Altarac et al. |
| 2012/0226315 A1 | 9/2012 | Altarac et al. |
| 2012/0232552 A1 | 9/2012 | Morgenstern Lopez et al. |
| 2012/0303039 A1 | 11/2012 | Chin et al. |
| 2012/0330359 A1 | 12/2012 | Kim |
| 2013/0012998 A1 | 1/2013 | Altarac et al. |
| 2013/0072985 A1 | 3/2013 | Kim |
| 2013/0165974 A1 | 6/2013 | Kim |
| 2013/0165975 A1 | 6/2013 | Tebbe et al. |
| 2013/0172932 A1 | 7/2013 | Altarac et al. |
| 2013/0172933 A1 | 7/2013 | Altarac et al. |
| 2013/0289399 A1 | 10/2013 | Choi et al. |
| 2013/0289622 A1 | 10/2013 | Kim |
| 2014/0081332 A1 | 3/2014 | Altarac et al. |
| 2014/0214082 A1 | 7/2014 | Reglos et al. |
| 2014/0358186 A1* | 12/2014 | Frock ................ A61B 17/8891 606/86 A |
| 2015/0150598 A1 | 6/2015 | Tebbe et al. |
| 2015/0150604 A1 | 6/2015 | Kim |
| 2015/0374415 A1 | 12/2015 | Kim |
| 2016/0030092 A1 | 2/2016 | Altarac et al. |
| 2016/0066963 A1 | 3/2016 | Kim |
| 2016/0242822 A1 | 8/2016 | Altarac et al. |
| 2016/0317193 A1 | 11/2016 | Kim |
| 2017/0071588 A1 | 3/2017 | Choi et al. |
| 2017/0128110 A1 | 5/2017 | Altarac et al. |
| 2017/0156763 A1 | 6/2017 | Altarac et al. |
| 2017/0245883 A1 | 8/2017 | Tebbe et al. |
| 2017/0258501 A1 | 9/2017 | Altarac et al. |
| 2017/0273722 A1 | 9/2017 | Altarac et al. |
| 2017/0296238 A1 | 10/2017 | Snell et al. |
| 2017/0348028 A1 | 12/2017 | Calvosa et al. |
| 2018/0028130 A1 | 2/2018 | Choi |
| 2018/0193064 A1 | 7/2018 | Kim |
| 2018/0228519 A1 | 8/2018 | Altarac et al. |
| 2019/0069933 A1 | 3/2019 | Altarac et al. |
| 2019/0090912 A1 | 3/2019 | Altarac et al. |
| 2019/0090913 A1 | 3/2019 | Altarac et al. |
| 2019/0105082 A1 | 4/2019 | Altarac et al. |
| 2019/0105083 A1 | 4/2019 | Kim |
| 2019/0201057 A1 | 7/2019 | Altarac et al. |
| 2021/0100592 A1 | 4/2021 | Seifert et al. |
| 2022/0054280 A1* | 2/2022 | Frock ................ A61B 17/7065 |
| 2022/0061894 A1 | 3/2022 | Altarac et al. |
| 2023/0240726 A1 | 8/2023 | Linares |
| 2023/0255786 A1* | 8/2023 | Lin ..................... A61F 2/4405 623/17.16 |
| 2024/0277384 A1* | 8/2024 | Malinowski ....... A61B 17/7065 |

FOREIGN PATENT DOCUMENTS

| | | |
|---|---|---|
| CN | 101897603 | 12/2010 |
| EP | 322334 | 6/1989 |
| EP | 0767636 | 1/1999 |
| EP | 0768843 | 2/1999 |
| EP | 1138268 | 10/2001 |
| EP | 1056408 | 12/2003 |
| EP | 1343424 | 9/2004 |
| EP | 1454589 | 9/2004 |
| EP | 1330987 | 3/2005 |
| EP | 1299042 | 3/2006 |
| EP | 1578314 | 5/2007 |
| EP | 1675535 | 5/2007 |
| EP | 0959792 | 11/2007 |
| EP | 1027004 | 12/2007 |
| EP | 1030615 | 12/2007 |
| EP | 1570793 | 5/2008 |
| EP | 1148850 | 4/2009 |
| EP | 1861046 | 2/2012 |
| FR | 2681525 | 3/1993 |
| FR | 2717675 | 5/1996 |
| FR | 2722980 | 9/1996 |
| FR | 2816197 | 5/2002 |
| SU | 988281 | 1/1983 |
| WO | WO9404088 | 3/1994 |
| WO | WO9426192 | 11/1994 |
| WO | WO9525485 | 9/1995 |
| WO | WO9531158 | 11/1995 |
| WO | WO9600049 | 1/1996 |
| WO | WO9829047 | 7/1998 |
| WO | WO9921500 | 5/1999 |
| WO | WO9921501 | 5/1999 |
| WO | WO9942051 | 8/1999 |
| WO | WO0013619 | 3/2000 |
| WO | WO0044319 | 8/2000 |
| WO | WO0044321 | 8/2000 |
| WO | WO0128442 | 4/2001 |
| WO | WO0191657 | 12/2001 |
| WO | WO0191658 | 12/2001 |
| WO | WO0203882 | 1/2002 |
| WO | WO0207623 | 1/2002 |
| WO | WO0207624 | 1/2002 |
| WO | WO02051326 | 7/2002 |
| WO | WO02067793 | 9/2002 |
| WO | WO02071960 | 9/2002 |
| WO | WO02076336 | 10/2002 |
| WO | WO03007791 | 1/2003 |
| WO | WO03007829 | 1/2003 |
| WO | WO03008016 | 1/2003 |
| WO | WO03015646 | 2/2003 |
| WO | WO03024298 | 3/2003 |
| WO | WO03045262 | 6/2003 |
| WO | WO03099147 | 12/2003 |
| WO | WO03101350 | 12/2003 |
| WO | WO04073533 | 9/2004 |
| WO | WO04110300 | 12/2004 |
| WO | WO05009300 | 2/2005 |
| WO | WO05013839 | 2/2005 |
| WO | WO05025461 | 3/2005 |
| WO | WO05041799 | 5/2005 |
| WO | WO05044152 | 5/2005 |
| WO | WO05055868 | 6/2005 |
| WO | WO05079672 | 9/2005 |
| WO | WO2005086776 | 9/2005 |
| WO | WO05115261 | 12/2005 |
| WO | WO06033659 | 3/2006 |
| WO | WO06034423 | 3/2006 |
| WO | WO06039243 | 4/2006 |
| WO | WO06039260 | 4/2006 |
| WO | WO06045094 | 4/2006 |
| WO | WO06063047 | 6/2006 |
| WO | WO06065774 | 6/2006 |
| WO | WO2006064356 | 6/2006 |
| WO | WO2006089085 | 8/2006 |
| WO | WO06102269 | 9/2006 |
| WO | WO06102428 | 9/2006 |
| WO | WO06102485 | 9/2006 |
| WO | WO06107539 | 10/2006 |
| WO | WO06110462 | 10/2006 |
| WO | WO06110464 | 10/2006 |
| WO | WO06110767 | 10/2006 |
| WO | WO06113080 | 10/2006 |
| WO | WO06113406 | 10/2006 |
| WO | WO06113814 | 10/2006 |
| WO | WO2006106246 | 10/2006 |

(56) References Cited

FOREIGN PATENT DOCUMENTS

| | | |
|---|---|---|
| WO | WO06118945 | 11/2006 |
| WO | WO06119235 | 11/2006 |
| WO | WO06119236 | 11/2006 |
| WO | WO06135511 | 12/2006 |
| WO | WO2007010140 | 1/2007 |
| WO | WO07015028 | 2/2007 |
| WO | WO07035120 | 3/2007 |
| WO | WO07075375 | 7/2007 |
| WO | WO07075788 | 7/2007 |
| WO | WO07075791 | 7/2007 |
| WO | WO07089605 | 8/2007 |
| WO | WO07089905 | 8/2007 |
| WO | WO07089975 | 8/2007 |
| WO | WO07097735 | 8/2007 |
| WO | WO07109402 | 9/2007 |
| WO | WO07110604 | 10/2007 |
| WO | WO07111795 | 10/2007 |
| WO | WO07111979 | 10/2007 |
| WO | WO07111999 | 10/2007 |
| WO | WO07117882 | 10/2007 |
| WO | WO07121070 | 10/2007 |
| WO | WO07127550 | 11/2007 |
| WO | WO07127588 | 11/2007 |
| WO | WO07127677 | 11/2007 |
| WO | WO07127689 | 11/2007 |
| WO | WO07127694 | 11/2007 |
| WO | WO07127734 | 11/2007 |
| WO | WO07127736 | 11/2007 |
| WO | WO07131165 | 11/2007 |
| WO | WO07134113 | 11/2007 |
| WO | WO2008009049 | 1/2008 |
| WO | WO08048645 | 4/2008 |
| WO | WO2008057506 | 5/2008 |
| WO | WO2008130564 | 10/2008 |
| WO | WO2009014728 | 1/2009 |
| WO | WO2009033093 | 3/2009 |
| WO | WO2009083276 | 7/2009 |
| WO | WO2009083583 | 7/2009 |
| WO | WO2009086010 | 7/2009 |
| WO | WO2009091922 | 7/2009 |
| WO | WO2009094463 | 7/2009 |
| WO | WO2009114479 | 9/2009 |
| WO | WO2011084477 | 7/2011 |
| WO | WO2015171814 | 11/2015 |

OTHER PUBLICATIONS

Choi, Gun et al., "Percutaneous Endoscopic Interlaminar Disectomy for Intracanalicular Disc Herniations at L5-S1 Using a Rigid Working Channel Endoscope," Operative Neurosurg., 58: pp. 59-68 (2006).
Fast, Avital et al., "Surgical Treatment of Lumbar Spinal Stenosis in the Elderly," Arch Phys. Med Rehabil., Mar. 1985, pp. 149-151, vol. 66.
Lee, Seungcheol et al., "New Surgical Techniques of Percutaneous Endoscopic Lumbar Disectomy for Migrated Disc Herniation," Joint Dis. Rel. Surg., 16(2); pp. 102-110 (2005).
Lee, Seungcheol et al., "Percutaneous Endoscopic Interlaminar Disectomy for L5-S1 Disc Herniation: Axillary Approach and Preliminary Results," J. of Korean Neurosurg. Soc., 40: pp. 79-83 (2006).
McCulloch, John A., Young, Paul H., "Essentials of Spinal Microsurgery," 1998, pp. 453-485. Lippincott-Raven Publishers, Philadelphia, PA (37 pages total).
Minns, R.J., et al., "Preliminary Design and Experimental Studies of a Noval Soft Implant for Correcting Sagittal Plane Instability in the Lumbar Spine," (1997) Spine, 22(16): 1819-1825.
Palmer, Sylvain et al., "Bilateral decompressive surgery in lumbar spinal stenosis associated with spondylolisthesis: unilateral approach and use of a microscope and tubular retractor system," Neurosurgery Focus, Jul. 2002, pp. 1-6, vol. 13.
Swan, Colby, "Point of View: Preliminary Design and Experimental Studies of a Novel Soft Implant for Correcting Sogittal Plane Instability in the Lumbar Spine," Spine, 1997, 22(16), 1826-1827.
Tredway, Trent L. et al., "Minimally Invasive Transforaminal Lumbar Interbody Fusion (MI-TLIF) and Lateral Mass Fusion with the MetRx System," (14 pages total), 2005.
Vaccaro, Alexander J. et al., MasterCases Spine Surgery, 2001, pp. 100-107. Thieme Medical Publishers, Inc., NY. (10 pages total).
Vertos mild Devices Kit—PRT-00430-C—Instructions for Use (13 pages total); see http://vertosmed.com/docs/mild1FU_PRT-00430-C.pdf., 2012.

\* cited by examiner

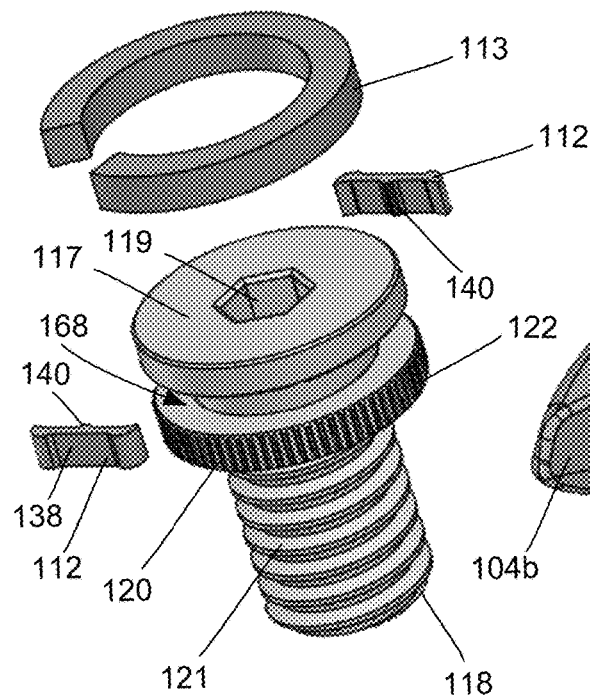
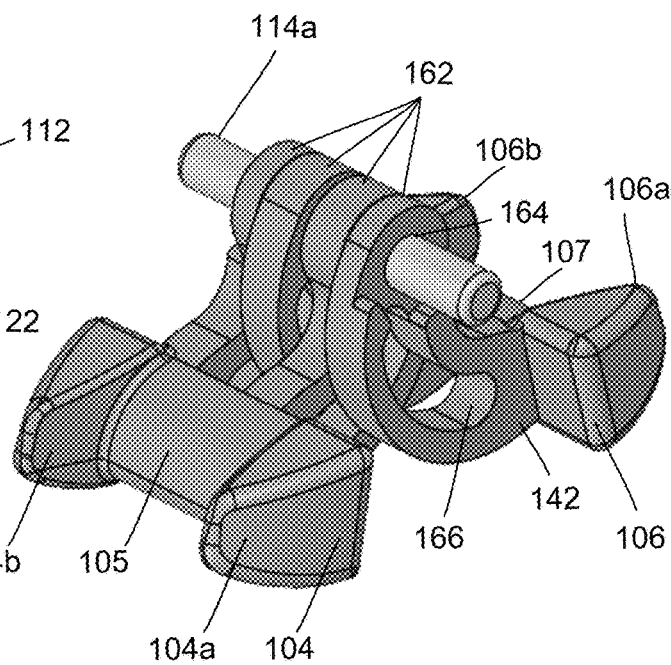
Fig. 2
Fig. 3
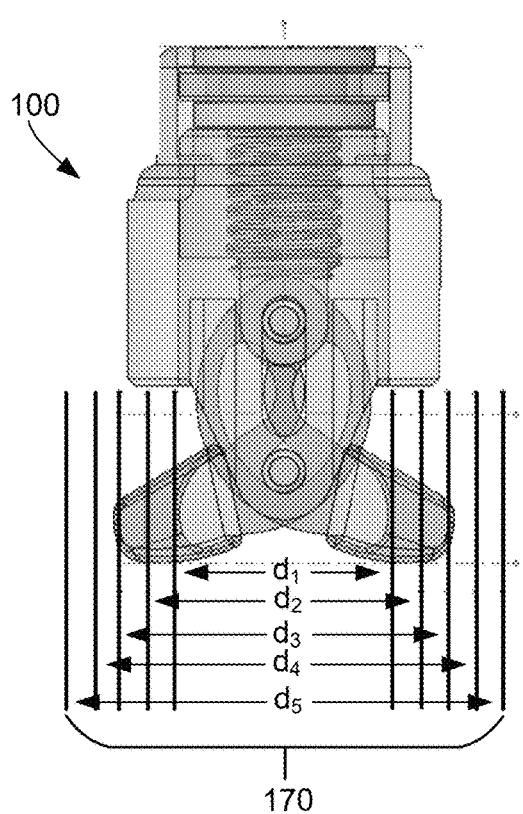
Fig. 4

INTERSPINOUS SPACER WITH A RANGE OF DEPLOYMENT POSITIONS AND METHODS AND SYSTEMS

CROSS-REFERENCE TO RELATED APPLICATIONS

This application claims the benefit under 35 U.S.C. § 119(e) of U.S. Provisional Patent Application Ser. No. 63/452,249, filed Mar. 15, 2023, which is incorporated herein by reference.

FIELD

The present invention is directed to the area of interspinous spacers for deployment between adjacent spinous processes. The present invention is also directed to systems and methods for utilizing the interspinous spacer.

BACKGROUND

With spinal stenosis, the spinal canal narrows and pinches the spinal cord and nerves, causing pain in the back and legs. Typically, with age, a person's ligaments may thicken, intervertebral discs may deteriorate, or facet joints may break down. The conditions can contribute to the narrowing of the spinal canal. Injury, heredity, arthritis, changes in blood flow, and other causes may also contribute to spinal stenosis.

Various treatments of the spine have been proposed or used including medications, surgical techniques, and implantable devices that alleviate and reduce pain associated with the back. In one surgical technique, a spacer is implanted between adjacent spinous processes of a patient's spine. The implanted spacer opens the spinal canal, maintains the desired distance between vertebral body segments, and, as a result, avoids or reduces impingement of nerves and relieves pain. For suitable candidates, an implantable interspinous spacer may provide significant benefits in terms of pain relief.

BRIEF SUMMARY

One aspect is an interspinous spacer that includes a body having a distal portion, a proximal portion, a proximal surface, a channel extending longitudinally from the proximal surface, and at least one slot extending longitudinally along the distal portion; an arm actuator defining a threaded channel extending longitudinally, wherein the arm actuator is configured to fit within the body; an actuator screw including a shaft having a proximal end and a distal portion, wherein the actuator screw further includes a head coupled to the proximal end of the shaft, wherein the distal portion of the shaft of the actuator screw is threaded and the actuator screw is at least partially disposed in the channel of the body and the threaded channel of the arm actuator, wherein, as the actuator screw is rotated using a driver tool, the arm actuator moves longitudinally relative to the body; a first pin, wherein the first pin is arranged to move along the at least one slot of the body; a second pin; and a first arm and a second arm, wherein each of the first and second arms includes a bridge, at least two receiving extensions extending from the bridge in a first direction and configured for receiving a portion of a vertebra therebetween, and a coupling extension extending from the bridge in a second direction, wherein each of the coupling extensions defines a pin opening and a curved track, wherein the first and second arms are coupled to the distal portion of the body by the second pin extending through the curved tracks of the coupling extensions and further coupled to the distal portion of the body and the actuator arm by the first pin extending through the pin openings of the coupling extensions, wherein the first and second arms are configured to rotate among different deployment positions according to the curved track in response to longitudinal movement of the actuator arm as the actuator screw is rotated.

In at least some aspects, the actuator screw further includes a disc disposed along the shaft distal to, and separated from, the head, wherein the shaft has an outer diameter that is smaller than outer diameters of the disc and the head. In at least some aspects, the disc includes a plurality of teeth arranged around a perimeter of the disc. In at least some aspects, the interspinous spacer further includes at least one locking inset positioned within the channel of the body for engagement by the disc of the actuator screw, each of the at least one locking inset including at least one tooth for interaction with the teeth of the disc to limit rotation of the actuator screw absent the driver tool. In at least some aspects, the interspinous spacer further includes a locking ring configured for engagement with the actuator screw between the head and the disc to limit movement of the actuator screw proximally or distally within the channel of the body, wherein the body defines a bounded groove within the channel to receive the locking ring, wherein the locking ring is a partial or full ring.

In at least some aspects, the interspinous spacer further includes each of the first arm and the second arm includes at least two of the coupling extensions. In at least some aspects, the interspinous spacer further includes the coupling extensions of the first arm interleave with the coupling extensions of the second arm.

In at least some aspects, the interspinous spacer further includes the body includes opposing undercut notches configured for receiving a clamp of a spacer insertion instrument. In at least some aspects, the interspinous spacer further includes the actuator screw further includes a shaped cavity formed in the head, wherein the shaped cavity is configured for receiving a bit of the driver tool that has a shape complementary to the shaped cavity.

Another aspect is an interspinous spacer that includes a body having a distal portion, a proximal portion, a proximal surface, and a channel extending longitudinally from the proximal surface; an arm actuator defining a threaded channel extending longitudinally, wherein the arm actuator is configured to fit within the body; an actuator screw including a shaft having a proximal end and a distal portion, a head coupled to the proximal end of the shaft, and a disc disposed along the shaft distal to, and separated from, the head, wherein the distal portion of the shaft of the actuator screw is threaded and the actuator screw is at least partially disposed in the channel of the body and the threaded channel of the arm actuator, wherein the disc includes a plurality of teeth arranged around a perimeter of the disc, wherein, as the actuator screw is rotated using a driver tool, the arm actuator moves longitudinally relative to the body; at least one locking inset positioned within the channel of the body for engagement by the disc of the actuator screw, each of the at least one locking inset including at least one tooth for interaction with the teeth of the disc to limit rotation of the actuator screw absent the driver tool; and a first arm and a second arm, wherein each of the first and second arms includes a bridge, at least two receiving extensions extending from the bridge in a first direction and configured for receiving a portion of a vertebra therebetween, and a coupling extension extending from the bridge in a second direction, wherein each of the coupling extensions is coupled to the distal portion of the body and the actuator arm.

In at least some aspects, the interspinous spacer further includes a locking ring configured for engagement with the actuator screw between the head and the disc to limit movement of the actuator screw proximally or distally within the channel of the body, wherein the body defines a bounded groove within the channel to receive the locking ring, wherein the locking ring is a partial or full ring. In at least some aspects, each of the first arm and the second arm includes at least two of the coupling extensions. In at least some aspects, the coupling extensions of the first arm interleave with the coupling extensions of the second arm.

In at least some aspects, the body further includes at least one slot extending longitudinally along the distal portion of the body, the interspinous spacer further including a first pin, wherein the first pin is arranged to move along the at least one slot of the body, wherein each of the coupling extensions defines a pin opening, wherein the first and second arms are coupled to the distal portion of the body and the actuator arm by the first pin extending through the pin openings of the coupling extension. In at least some aspects, the interspinous spacer further includes a second pin, wherein each of the coupling extensions further defines a curved track, wherein the first and second arms are coupled to the distal portion of the body by the second pin through the curved tracks of the coupling extensions, wherein the first and second arms are configured to rotate relative to the body according to the curved track in response to longitudinal movement of the actuator arm as the actuator screw is rotated.

In at least some aspects, the at least one locking inset includes two locking insets disposed opposite each other. In at least some aspects, the body includes opposing undercut notches configured for receiving a clamp of a spacer insertion instrument. In at least some aspects, the actuator screw further includes a shaped cavity formed in the head, wherein the shaped cavity is configured for receiving a bit of the driver tool that has a shape complementary to the shaped cavity.

Yet another aspect is a kit that includes any of the interspinous spacers described above; a spacer insertion instrument configured to releasably grip the interspinous spacer for implantation into a patient; and the driver tool having a spacer engaging bit configured to engage the actuator screw of the interspinous spacer and rotate the actuator screw by rotation of the driver tool.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 2 is schematic perspective side view of an actuator screw, locking inserts, and locking ring of the interspinous spacer of FIG. 1A;

FIG. 3 is schematic perspective side view of arms and a pin of the interspinous spacer of FIG. 1A;

FIG. 4 is schematic side view of the interspinous spacer of FIG. 1A illustrating different separation distances, represented by vertical lines, for the arms;

DETAILED DESCRIPTION

Figure 1A:
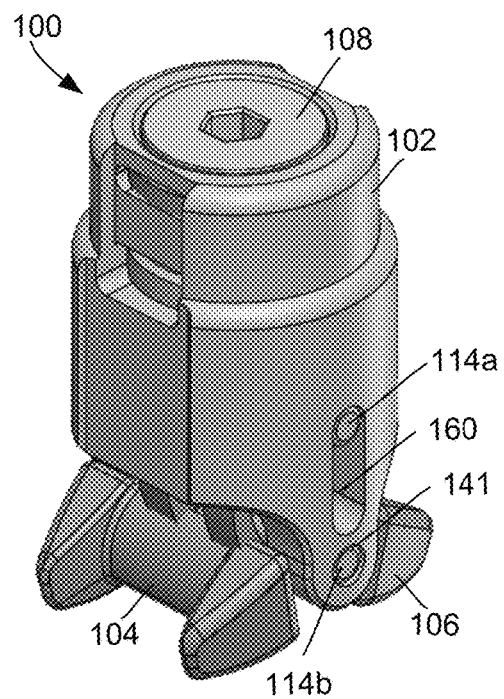
FIG. 1A is a schematic perspective view of one embodiment of an interspinous spacer in a first deployed position.

The present invention is directed to the area of interspinous spacers for deployment between adjacent spinous processes. The present invention is also directed to systems and methods for utilizing the interspinous spacer.

Examples of interspinous spacers are found in U.S. Pat. Nos. 8,123,782; 8,128,662; 8,273,108; 8,277,488; 8,292,922; 8,425,559; 8,613,747; 8,864,828; 9,119,680; 9,155,572; 9,161,783; 9,393,055; 9,532,812; 9,572,603; 9,861,398; 9,956,011; 10,080,587; 10,166,047; 10,610,267; 10,653,456; 10,835,295; 10,835,297; 11,013,539; and 11,229,461, all of which are incorporated herein by reference. Unless indicated otherwise, the features and methods described in these references can be applied to the interspinous spacers described herein.

Conventional interspinous spacers typically have a fixed distance between the two arms when deployed. Conventionally, interspinous spacers of different sizes are available and the clinician selects which size is to be used for a particular surgery based on the size and arrangement of the vertebrae.

In addition, in at least some conventional interspinous spacers, a spindle arrangement is provided for engagement by a tool and rotation using the tool to cause the arms of the spacer to rotate for engagement with the vertebrae (for example the spinous processes of the adjacent vertebrae). The spindle arrangement is welded to the body of the interspinous spacer.

As described herein, a single interspinous spacer can have a range of deployment positions (for example, provide for a range of distances between the two arms when deployed). This allows the interspinous spacer to fit a range of different spacings between adjacent vertebrae. Additionally or alternatively, an interspinous spacer can utilize an actuator screw instead of a spindle arrangement, as described herein.

FIGS. 1A, 1B, 1C, 2, 3, and 4 illustrate one embodiment of an interspinous spacer 100 that includes a body 102, a first (or superior) arm 104, a second (or inferior) arm 106, an actuator screw 108, two locking inserts 112, a locking ring 113, a first pin 114a, a second pin 114b, and an arm actuator 115. There is no weld between the body 102 and the actuator screw 108.

Figure 1B:
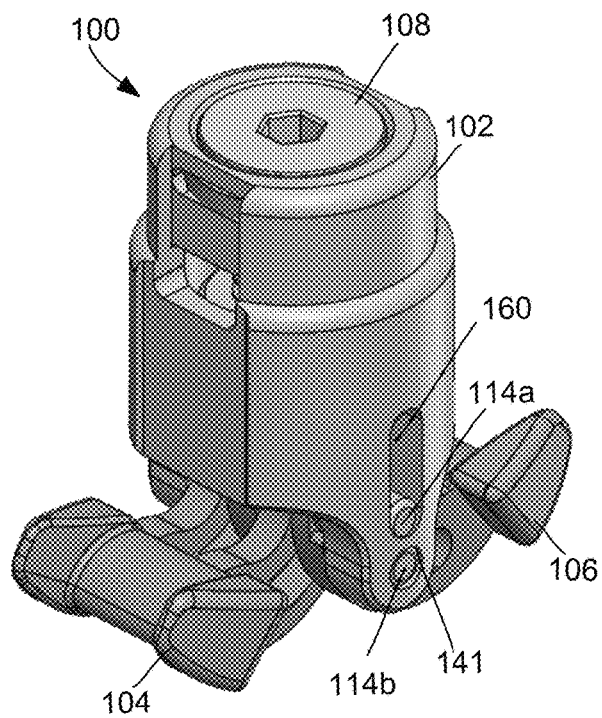
FIG. 1B is a schematic perspective view of the interspinous spacer of FIG. 1A in a second deployed position.

In FIG. 1A, the first and second arms 104, 106 of the spacer 100 are in a first deployed position with the first and second arms 104, 106 separated by a first distance (for example, 8 mm). In FIG. 1B, the first and second arms 104, 106 of the spacer 100 are in a second deployed position with the first and second arms 104, 106 separated by a second distance (for example, 16 mm). In this embodiment, the first and second arms 104, 106 has a range of deployment positions from the first deployed position to the second deployed position. The first and second arms 104, 106 can be separated by any distance in the range from the first distance to the second distance (for example, any distance from 8 to 16 mm). This allows the spacer 100 to fit a range of different spacings between adjacent vertebrae.

The first arm 104 includes two receiving extensions 104a, 104b coupled by a bridge 105 from which an attachment portion 142 extends. The second arm 106 includes two receiving extensions 106a, 106b coupled by a bridge 107 from which the attachment portion 142 extends. In each deployment position, the pairs of receiving extensions 104a, 104b, 106a, 106b extend away from the body 102 of the spacer 100 with the extensions of each pair disposed on opposing sides of one of the adjacent vertebrae (for example, the spinous process of the adjacent vertebra), as illustrated in FIGS. 1A and 1B. The first and second arms 104, 106 of the spacer 100 are not necessarily perpendicular to the longitudinal axis of the body 102. Instead, the angle of the first and second arms 104, 106 of the spacer 100 relative to the longitudinal axis of the body 102 depends on the selected deployed position which can range from the first deployed position of FIG. 1A to the second deployed position of FIG. 1B. In at least some embodiments, the shape of the bridges 105, 107 is selected to provide suitable engagement of the adjacent vertebrae for the range of selectable deployed positions.

In at least some embodiments, the length of the bridge 105 of the first arm 104 is approximately 7 to 10 millimeters and the length of the bridge 107 of the second arm 106 is approximately 5 to 8 millimeters. In at least some embodiments, the tip-to-tip distance of the extensions 104a, 104b is approximately 8 to 12 millimeters and the tip-to-tip distance of the extensions 106a, 106b is approximately 8 to 12 millimeters. In at least some embodiments, the first arm 104 forms a larger space for receiving the superior vertebra (for example, the superior spinous process) than the space formed by the second arm 106 for receiving the inferior vertebra (for example, the inferior spinous process) as vertebrae and spinous processes are naturally narrower on top and wider on the bottom. In at least some embodiments, where there is a difference in size between the first and second arms 104, 106, the spacer 100 may include a marking or other indication so that a clinician can individually identify the first and second arms 104, 106 for correct implantation orientation within the patient.

In at least some other embodiments, the first and second arms 104, 106 form a same-sized space for receiving the vertebrae. In at least some embodiments, the bridges 105, 107 of the first and second arms 104, 106 have a same length.

Figure 1C:
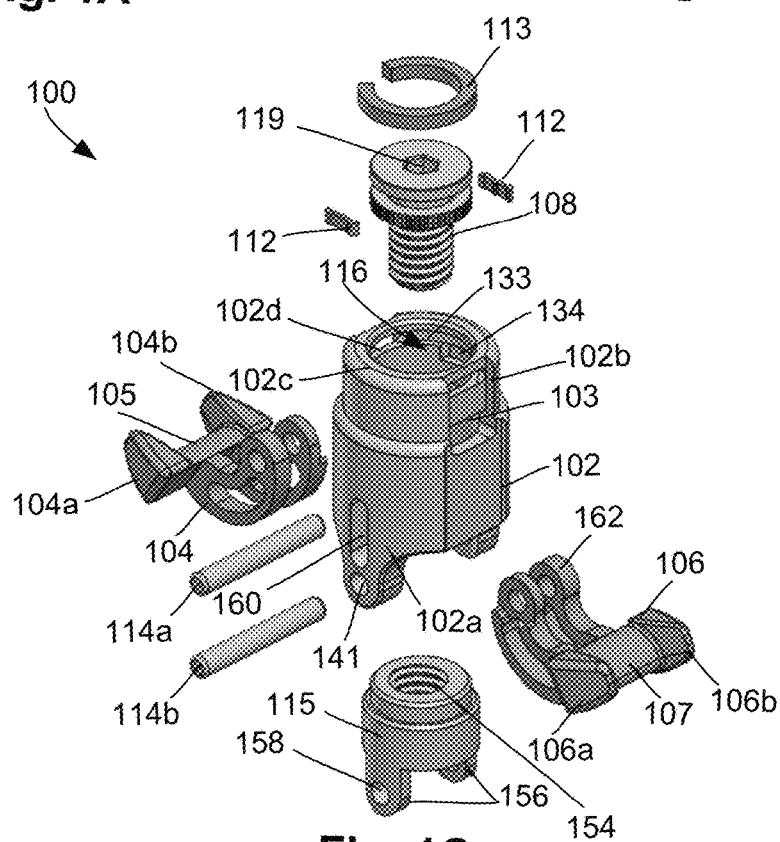
FIG. 1C is a schematic perspective exploded view of the interspinous spacer of FIG. 1A.
Figure 5:
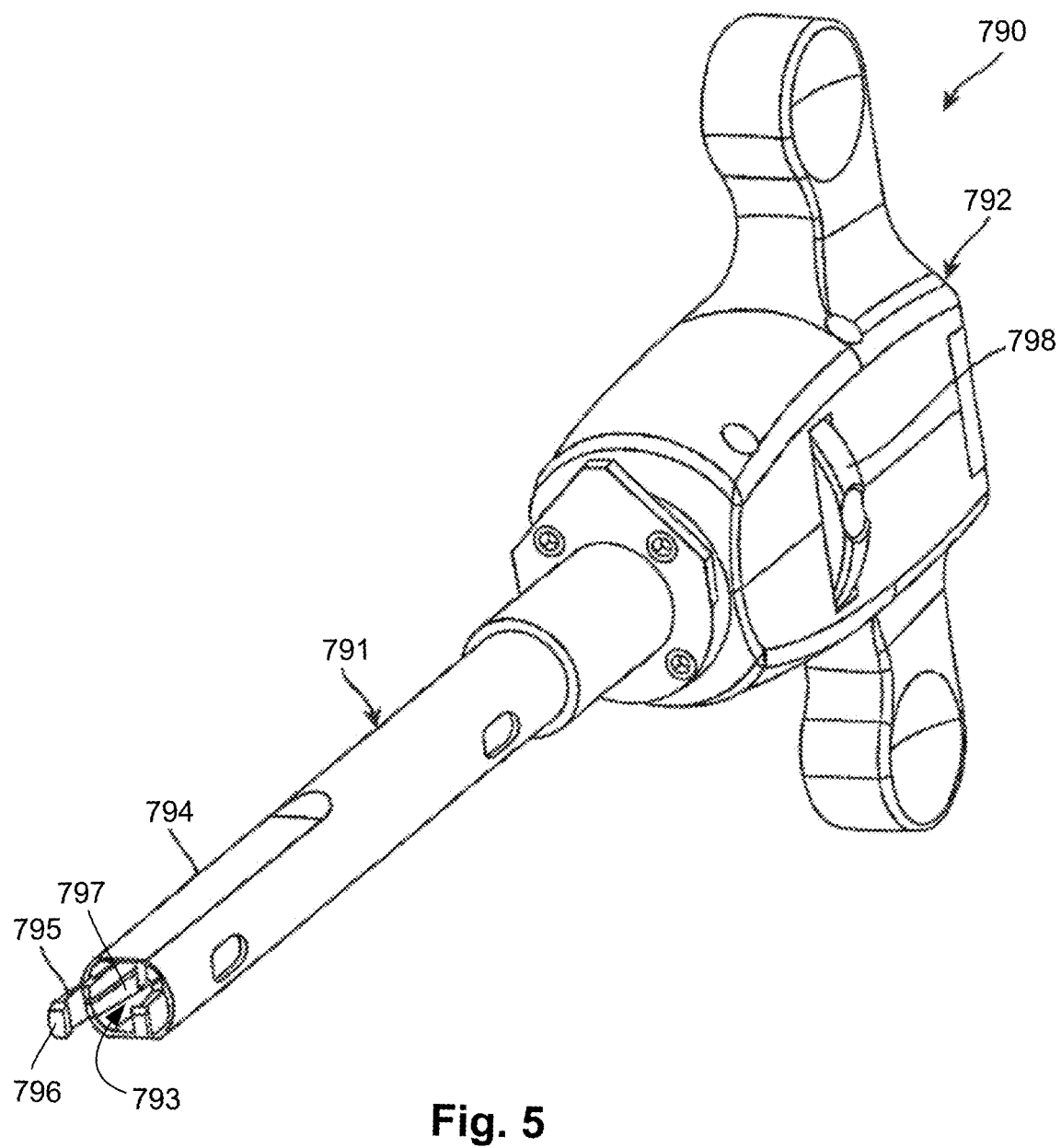
FIG. 5 is a perspective view of one embodiment of a spacer insertion instrument.

The body 102 includes a distal portion 102a, a proximal portion 102b, a proximal surface 102c, and an opening 102d in the proximal surface for the actuator screw 108. The body 102 defines a channel 116 that extends distally from the opening 102d through at least a portion of the body 102, as illustrated in FIG. 1C. In at least some embodiments, the body 102 includes undercut notches 103 formed on opposite sides of the proximal portion 102b of the body. In at least some embodiments, the notches 103 are configured for attachment of clamps 795 of a spacer insertion instrument 790 (FIG. 5).

The body 102 includes opposing slots 160 (or at least one slot) for receiving a first pin 114a and travel of the first pin along the slots as the first and second arms 104, 106 are deployed or retracted. The body 102 also includes opposing pin holes 141, distal of the opposing slots 160, for receiving a second pin 114b.

The actuator screw 108 includes a head 117, a shaft 118, and a disc 120 disposed along the shaft and having teeth 122 arranged around the perimeter of the disc, as illustrated in FIG. 2. The disc 120 has a larger outer diameter than the shaft 118 and is positioned distal to the head 117 with a gap 168 between the disc and the head. At least a portion 121 of the shaft 118 distal to the disc is threaded. The actuator screw 108 can be made from a single piece of material or may contain two or more components that are attached together. The head 117 of the actuator screw 108 includes a shaped cavity 119 to receive a driver tool 880 (FIG. 6) with a complementary-shaped engaging bit 884. Engagement of the actuator screw 108 by the driver tool allows a user to rotate the actuator screw to further separate (or, in at least some embodiments, retract) the first and second arms 104, 106.

A locking ring 113 fits on the actuator screw 108 in the gap 168 between the head 117 and the disc 120. As the actuator screw 108 is inserted into the channel 116 of the body 102, the locking ring 113 fits within a bounded groove 133 in the interior wall of the body. The locking ring 113 resists movement of the actuator screw 108 up or down (e.g., distally or proximally) within the body 102. The locking ring 113 can be a full ring or a partial ring (as illustrated in FIG. 1C).

Figure 6:
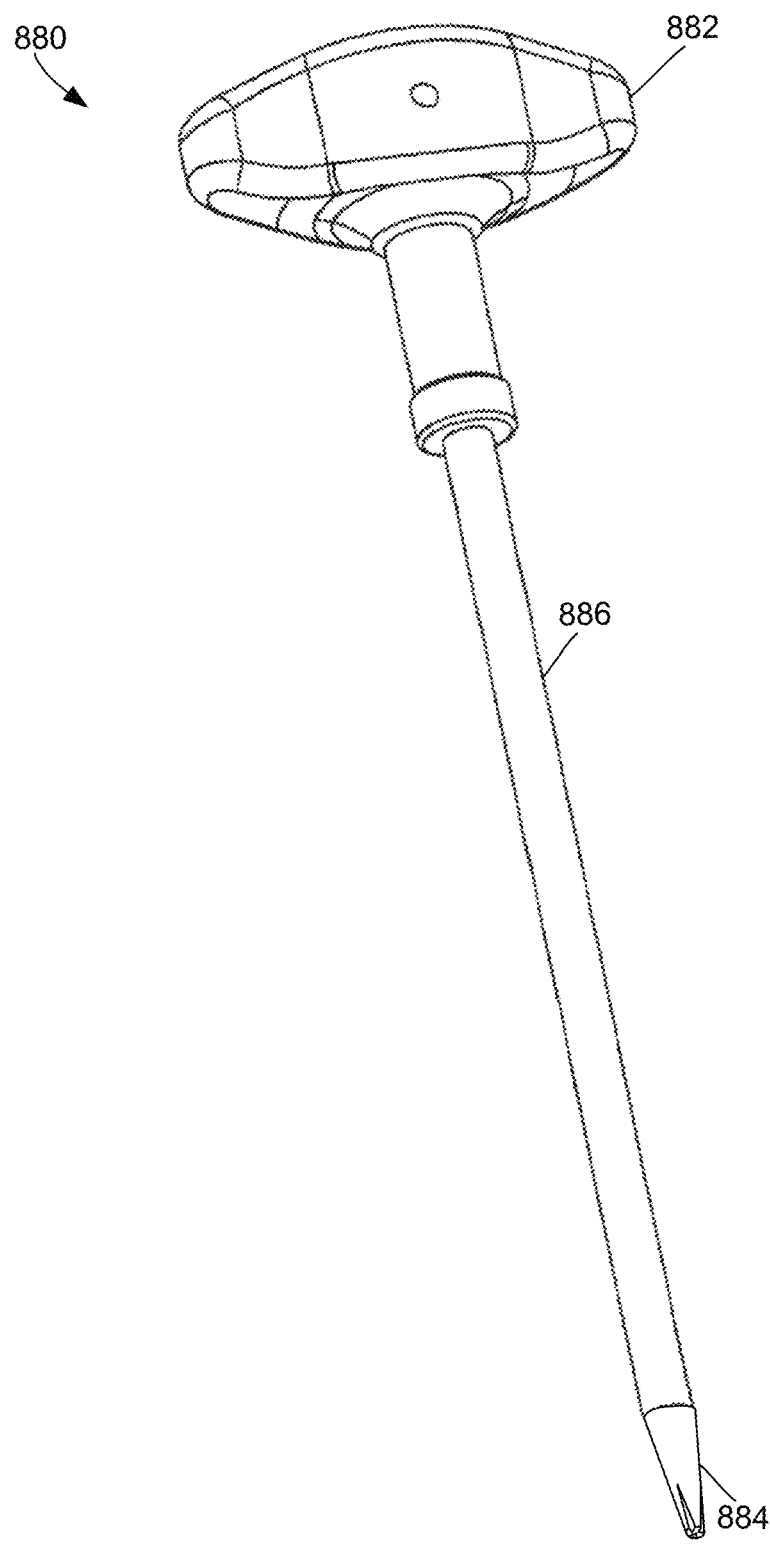
FIG. 6 is a perspective view of one embodiment of a driver tool.

Locking insets 112 fit within opposing indents 134 located below the bounded groove 133 in the interior wall of the body 102 so that the locking insets 112 are exposed within the body. Each locking inset 112 includes a body 138 and at least one tooth 140 (FIG. 2) extending from the body. The at least one tooth 140 of the locking inset 112 is arranged to engage the teeth 122 of the disc 120 of the actuator screw 108 when the actuator screw is disposed within the body 102. The at least one tooth 140 of the locking insets 112 and the teeth 122 of the disc 120 of the actuator screw 108 are arranged to resist rotation of the actuator screw except by use of a tool 880 (FIG. 6) that engages the actuator screw 108. In at least some embodiments, the shape and size of the at least one tooth 140 of the locking insets 112 and the teeth 122 of the disc 120 of the actuator screw 108 are selected to resist rotation of the actuator screw when the first and second arms 104, 106 are separated at a selected deployment position and force is applied to the first and second arms 104, 106 such as, for example, during the patient's movement and bending. In at least some embodiments, the shape and size of the at least one tooth 140 of the locking insets 112 and the teeth 122 of the disc 120 of the actuator screw 108 are selected to generate a clicking sound as the actuator screw 108 is rotated using a tool 880 (FIG. 6).

The arm actuator 115 includes a threaded channel 154 into which the threaded portion 121 of the shaft 118 of the actuator screw 108 extends. The threads and the size of the threaded channel 154 of the arm actuator 115 and the threaded shaft 118 of the actuator screw 108 are complementary so that the actuator screw 108 fits within the threaded channel 154 and moves distally or proximally, along a path defined by the threads, as the actuator screw 108 is rotated. The arm actuator 115 further includes two opposing actuator extensions 156 that each define a pin opening 158 for receiving the first pin 114a.

Each of the first and second arms 104, 106 includes at least one coupling extension 162 extending from the bridge 105, 107. Each coupling extension 162 defines an opening 164 for receiving the first pin 114a, as illustrated in FIG. 3, and a curved track 166 for receiving the second pin 114b and allowing the second pin to move along the curved track in response to rotation of the actuator screw 108. In the illustrated embodiment of FIGS. 1A, 1B, 1C, and 3, each of the first and second arms 104, 106 includes two coupling extensions 162 that, when the spacer 100 is assembled, interleave with each other as illustrated in FIG. 3. When the spacer 100 is assembled, the first pin 114a passes through the opposing slots 160 of the body 102, the pin openings 158 of the arm actuator 115, and the openings 164 of the coupling extensions 162 of the first and second arms 104, 106. The second pin 115b passes through the opposing pin holes 141 of the body 102 and the curved tracks 166 of the coupling extensions 162 of the first and second arms 104, 106.

As the actuator screw 108 is rotated in a first direction, the arm actuator 115 moves distally. The first pin 114a is carried distally by the arm actuator 115 pushing the portions of the first and second arms 104, 106 adjacent to the first pin 114a distally. This causes the first and second arms 104, 106 to rotate about the second pin 114b according to the path of the curved tracks 166 of the first and second arms 104, 106 resulting in the first and second arms separating from each other, as illustrated by comparing FIGS. 1A and 1B.

Rotating the actuator screw 108 in a second direction, opposite the first direction, reverses the movement of the arm actuator 115, pin 114a, and first and second arms 104, 106. The ends of the opposing slots 160 of the body 102 limit movement of the first pin 114a and, thereby, limit the range of separation of the first and second arms 104, 106.

In the first deployed position of FIG. 1A, the first pin 114a is at the most proximal position along opposing slots 160 in the body 102. In the first deployed position of FIG. 1B, the first pin 114a is at the most distal position along the opposing slots 160 in the body 102. FIG. 4 illustrates examples of different separation distances 170 (representing different deployed positions) between the first and second arms 104, 106 for one embodiment of the spacer 100. Examples of separation distances are illustrated in FIG. 4 as $d_1$, $d_2$, $d_3$, $d_4$, and $d_5$ (for example, 8, 10, 12, 14, or 16 mm, respectively). In at least some embodiments, any distance between the largest and smallest separation distance can be achieved. In at least some embodiments, the selectable distances may be defined in part by the teeth 122 on the disc 120 of the actuator screw 118, as well as the length of the opposing slots 160 of the body 102.

U.S. Pat. Nos. 8,123,782; 8,128,662; 8,273,108; 8,277,488; 8,292,922; 8,425,559; 8,613,747; 8,864,828; 8,945,183; 9,119,680; 9,155,572; 9,161,783; 9,393,055; 9,532,812; 9,572,603; 9,861,398; 9,956,011; 10,080,587; 10,166,047; 10,610,267; 10,653,456; 10,835,295; 10,835,297; 11,013,539; and 11,229,461, all of which are incorporated herein by reference, illustrate a variety of tools for insertion and deployment of a spacer between adjacent spinous processes. These tools can be used or modified for insertion and deployment of the spacer 100 described above.

As an example, FIGS. 5 and 6 illustrate a spacer insertion instrument 790 and a driver tool 880, respectively. The spacer insertion instrument 790 includes a cannula 791 connected to a handle 792. The spacer insertion instrument 790 defines a central passageway 793 through the handle 792 and cannula 791. The driver tool 880 is removably insertable into the central passageway 793.

The cannula 791 includes clamps (for example, prongs) 795 to releasably clamp to the body 102 of the spacer 100 (for example, to the undercut notches 103 formed on opposite sides of the body 102) for delivery of the spacer into the patient using the spacer insertion instrument 790. In at least some embodiments, the clamps 795 include extensions 796 that extend inwardly toward each other to form hooks. In at least some embodiments, the extensions 796 can engage the undercut notches 103 (FIG. 1C) formed on opposite sides of the body 102 of the spacer 100 to grip the spacer.

The cannula 791 also includes an inner shaft 797 (to which the clamps 795 are attached), an outer shaft 794, and a control 798. In at least some embodiments, the inner shaft 797 is connected to the handle 792 and the outer shaft 794 is passed over the inner shaft 797.

The outer shaft 794 translates with respect to the inner shaft 797 (or, alternatively, the inner shaft translates with respect to the outer shaft) using the control 798. The translation of the outer shaft 794 (or the inner shaft 797) operates the clamps 795. When the outer shaft 794 moves away from the clamps 795, the clamps separate to allow loading (or unloading) of the spacer 100 on the spacer insertion instrument 790. When the outer shaft 794 moves toward the clamps 795, the clamps are moved together to grip the spacer 100. For example, the clamps 795 can grip the undercut notches 103 formed on opposite sides of the body 102 of the spacer 100. In this manner, the spacer insertion instrument 790 can hold the spacer 100 for delivery of the spacer into position between adjacent spinous processes within the patient.

Turning to FIG. 8, a driver tool 880 includes a handle 882 at the proximal end and a spacer engaging bit 884 (for example, a socket key or hexagonal tip) at the distal end. The handle 882 and spacer engaging bit 884 are connected by a shaft 886. The driver tool 880 is sized to be inserted into the central passageway 793 of the spacer insertion instrument 790 such that the spacer engaging bit 884 at the distal end operatively connects with a spacer 100 gripped by the clamps 795 of the spacer insertion instrument 790. The spacer engaging bit 884 includes features for engaging with the shaped cavity 119 (see, for example. FIG. 2) in the actuator screw 108 of the spacer 100. In at least some embodiments, the driver tool 880 has a spacer engaging bit 884 that is complementary to the shaped cavity 119 in the actuator screw 108 of the spacer 100. For example, the bit 884 can have a flat (like a regular screwdriver), cross (like a Phillips screwdriver), square, pentagonal, hexagonal, or octagonal shape (or any other suitable shape) with the shaped cavity 119 having a complementary shape. Rotating the driver tool 880 when engaged with the actuator screw 108 of the spacer 100 rotates the actuator screw 108 to separate the arms 104, 106 of the spacer, as described above.

In at least some embodiments, a small midline or lateral-to-midline incision is made in the patient for percutaneous delivery of the spacer 100. In at least some embodiments, the supraspinous ligament is avoided. In at least some embodiments, the supraspinous ligament is split longitudinally along the direction of the tissue fibers to create an opening for the instrument. In at least some embodiments, one or more dilators may be used to create or enlarge the opening.

In at least some embodiments, the spacer 100, in the first deployed position, is releasably attached to the spacer insertion instrument 790 as described above. In at least some embodiments, the spacer 100 is inserted into a port or cannula, if one is employed, which has been operatively positioned to form an opening to the interspinous space within a patient's back. The spacer 100, attached to the spacer insertion instrument 790, is inserted into the interspinous space between the spinous processes of two adjacent vertebral bodies. In at least some embodiments, the spacer 100 is advanced beyond the end of a cannula or, alternatively, the cannula is pulled proximately to uncover the spacer 100 connected to the spacer insertion instrument 790. Once in position, the driver tool 880 is inserted into the spacer insertion instrument 790, if not previously inserted, to engage the actuator screw 108. The driver tool 880 is rotated to rotate the actuator screw 108. The rotating actuator screw 108 changes the deployed position of the spacer 100. Rotation in one direction, for example, clockwise, for example, increase the separation distance between the arms 104, 106 (compare, for example, FIGS. 1A and 1B).

The arms 104, 106 of the spacer may be positioned in one of many deployed positions with different separation distances. In at least some, embodiments, the separation of the arms 104, 106 can be reversed by rotating the actuator screw 108 in the opposite direction, for example, counterclockwise.

In at least some embodiments, a clinician can observe with fluoroscopy or other imaging technique the positioning of the spacer 100 inside the patient and then choose to reposition the spacer 100, if desired. Repositioning of the spacer may involve reversing, or partially reversing, the separation of the arms 104, 106. The spacer 100 may then be re-deployed into the desired location. This process can be repeated as necessary until the clinician has achieved the desired positioning of the spacer in the patient.

Following deployment of the spacer, the spacer insertion instrument 790 and driver tool 880 (and any other instrumentation, such as a cannula or dilator) is removed from the body of the patient. The spacer insertion instrument 790 can be operated as described above to release the clamps 795 from the spacer 100.

The above specification provides a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. An interspinous spacer, comprising:
   a body having a distal portion, a proximal portion, a proximal surface, a channel extending longitudinally from the proximal surface, and at least one slot extending longitudinally along the distal portion;
   an arm actuator defining a threaded channel extending longitudinally, wherein the arm actuator is configured to fit within the body;
   an actuator screw comprising a shaft having a proximal end and a distal portion, wherein the actuator screw further comprises a head coupled to the proximal end of the shaft, wherein the distal portion of the shaft of the actuator screw is threaded and the actuator screw is at least partially disposed in the channel of the body and the threaded channel of the arm actuator, wherein, as the actuator screw is rotated using a driver tool, the arm actuator moves longitudinally relative to the body;
   a first pin, wherein the first pin is arranged to move along the at least one slot of the body;
   a second pin; and
   a first arm and a second arm, wherein each of the first and second arms comprises a bridge, at least two receiving extensions extending from the bridge in a first direction and configured for receiving a portion of a vertebra therebetween, and a coupling extension extending from the bridge in a second direction, wherein each of the coupling extensions defines a pin opening and a curved track, wherein the first and second arms are coupled to the distal portion of the body by the second pin extending through the curved tracks of the coupling extensions and further coupled to the distal portion of the body and the arm actuator by the first pin extending through the pin openings of the coupling extensions, wherein the first and second arms are configured to rotate among different deployment positions according to the curved track in response to longitudinal movement of the arm actuator as the actuator screw is rotated.

2. The interspinous spacer of claim 1, wherein the actuator screw further comprises a disc disposed along the shaft distal to, and separated from, the head, wherein the shaft has an outer diameter that is smaller than outer diameters of the disc and the head.

3. The interspinous spacer of claim 2, wherein the disc comprises a plurality of teeth arranged around a perimeter of the disc.

4. The interspinous spacer of claim 3, further comprising at least one locking inset positioned within the channel of the body for engagement by the disc of the actuator screw, each of the at least one locking inset comprising at least one tooth for interaction with the teeth of the disc to limit rotation of the actuator screw absent the driver tool.

5. The interspinous spacer of claim 3, further comprising a locking ring configured for engagement with the actuator screw between the head and the disc to limit movement of the actuator screw proximally or distally within the channel of the body, wherein the body defines a bounded groove within the channel to receive the locking ring, wherein the locking ring is a partial or full ring.

6. The interspinous spacer of claim 1, wherein each of the first arm and the second arm comprises at least two of the coupling extensions.

7. The interspinous spacer of claim 6, wherein the coupling extensions of the first arm interleave with the coupling extensions of the second arm.

8. The interspinous spacer of claim 1, wherein the body comprises opposing undercut notches configured for receiving a clamp of a spacer insertion instrument.

9. The interspinous spacer of claim 1, wherein the actuator screw further comprises a shaped cavity formed in the head, wherein the shaped cavity is configured for receiving a bit of the driver tool that has a shape complementary to the shaped cavity.

10. A kit, comprising:
    the interspinous spacer of claim 1;
    a spacer insertion instrument configured to releasably grip the interspinous spacer for implantation into a patient; and
    the driver tool comprising a spacer engaging bit configured to engage the actuator screw of the interspinous spacer and rotate the actuator screw by rotation of the driver tool.

11. An interspinous spacer, comprising:
    a body having a distal portion, a proximal portion, a proximal surface, and a channel extending longitudinally from the proximal surface;
    an arm actuator defining a threaded channel extending longitudinally, wherein the arm actuator is configured to fit within the body;
    an actuator screw comprising a shaft having a proximal end and a distal portion, a head coupled to the proximal end of the shaft, and a disc disposed along the shaft distal to, and separated from, the head, wherein the distal portion of the shaft of the actuator screw is threaded and the actuator screw is at least partially disposed in the channel of the body and the threaded channel of the arm actuator, wherein the disc comprises a plurality of teeth arranged around a perimeter of the disc, wherein, as the actuator screw is rotated using a driver tool, the arm actuator moves longitudinally relative to the body;

at least one locking inset positioned within the channel of the body for engagement by the disc of the actuator screw, each of the at least one locking inset comprising at least one tooth for interaction with the teeth of the disc to limit rotation of the actuator screw absent the driver tool; and a first arm and a second arm, wherein each of the first and second arms comprises a bridge, at least two receiving extensions extending from the bridge in a first direction and configured for receiving a portion of a vertebra therebetween, and a coupling extension extending from the bridge in a second direction, wherein each of the coupling extensions is coupled to the distal portion of the body and the arm actuator.

12. The interspinous spacer of claim 11, further comprising a locking ring configured for engagement with the actuator screw between the head and the disc to limit movement of the actuator screw proximally or distally within the channel of the body, wherein the body defines a bounded groove within the channel to receive the locking ring, wherein the locking ring is a partial or full ring.

13. The interspinous spacer of claim 11, wherein each of the first arm and the second arm comprises at least two of the coupling extensions.

14. The interspinous spacer of claim 13, wherein the coupling extensions of the first arm interleave with the coupling extensions of the second arm.

15. The interspinous spacer of claim 11, wherein the body further comprises at least one slot extending longitudinally along the distal portion of the body, the interspinous spacer further comprising a first pin, wherein the first pin is arranged to move along the at least one slot of the body, wherein each of the coupling extensions defines a pin opening, wherein the first and second arms are coupled to the distal portion of the body and the arm actuator by the first pin extending through the pin openings of the coupling extensions.

16. The interspinous spacer of claim 15, further comprising a second pin, wherein each of the coupling extensions further defines a curved track, wherein the first and second arms are coupled to the distal portion of the body by the second pin through the curved tracks of the coupling extensions, wherein the first and second arms are configured to rotate relative to the body according to the curved track in response to longitudinal movement of the arm actuator as the actuator screw is rotated.

17. The interspinous spacer of claim 11, wherein the at least one locking inset comprises two locking insets disposed opposite each other.

18. The interspinous spacer of claim 11, wherein the body comprises opposing undercut notches configured for receiving a clamp of a spacer insertion instrument.

19. The interspinous spacer of claim 11, wherein the actuator screw further comprises a shaped cavity formed in the head, wherein the shaped cavity is configured for receiving a bit of the driver tool that has a shape complementary to the shaped cavity.

20. A kit, comprising:
the interspinous spacer of claim 11;
a spacer insertion instrument configured to releasably grip the interspinous spacer for implantation into a patient; and
the driver tool comprising a spacer engaging bit configured to engage the actuator screw of the interspinous spacer and rotate the actuator screw by rotation of the driver tool.

* * * * *